(12) United States Patent
Hanyu et al.

(10) Patent No.: US 8,563,552 B2
(45) Date of Patent: *Oct. 22, 2013

(54) WHITENING AGENT AND SKIN EXTERNAL PREPARATION

(75) Inventors: Naoto Hanyu, Yokohama (JP); Tomoko Saito, Yokohama (JP); Takako Shibata, Yokohama (JP); Kiyoshi Sato, Yokohama (JP); Kimihiro Ogino, Yokohama (JP)

(73) Assignee: Shiseido Company Ltd., Chuo-ku, Tokyo (JP)

(*) Notice: Subject to any disclaimer, the term of this patent is extended or adjusted under 35 U.S.C. 154(b) by 393 days.

This patent is subject to a terminal disclaimer.

(21) Appl. No.: 12/866,250

(22) PCT Filed: Feb. 6, 2009

(86) PCT No.: PCT/JP2009/052077
§ 371 (c)(1),
(2), (4) Date: Aug. 5, 2010

(87) PCT Pub. No.: WO2009/099193
PCT Pub. Date: Aug. 13, 2009

(65) Prior Publication Data
US 2011/0003817 A1 Jan. 6, 2011

(30) Foreign Application Priority Data

Feb. 8, 2008 (JP) .................. 2008-029106
Aug. 1, 2008 (JP) .................. 2008-199606

(51) Int. Cl.
*A61K 31/535* (2006.01)

(52) U.S. Cl.
USPC ........ 514/236.5; 514/275; 514/406; 514/341; 544/122; 544/330; 546/275.4; 548/377.1

(58) Field of Classification Search
USPC ............... 514/236.5, 275, 406, 341; 544/330, 544/122; 546/275.4; 548/377.1
See application file for complete search history.

(56) References Cited

U.S. PATENT DOCUMENTS

| 7,705,041 B2 | 4/2010 | Michelet et al. |
| 2007/0243132 A1 | 10/2007 | Russell-Jones et al. |
| 2009/0036475 A1 | 2/2009 | Eriksen et al. |

FOREIGN PATENT DOCUMENTS

| EP | 0234104 | * | 9/1987 |
| EP | 0264883 | * | 4/1988 |
| EP | 0278610 | * | 8/1988 |
| EP | 0841326 | * | 5/1998 |
| EP | 1437348 | | 7/2004 |
| JP | 42-19593 | | 10/1942 |
| JP | 54-117029 | | 9/1979 |
| JP | 54-147921 | | 11/1979 |
| JP | 62-404 | | 1/1987 |
| WO | 02/069910 | | 10/2002 |
| WO | WO2005028467 | * | 3/2005 |
| WO | 2006/100212 | | 9/2006 |
| WO | 2006/133876 A1 | | 12/2006 |
| WO | 2007/070983 | | 6/2007 |

OTHER PUBLICATIONS

Kinugawa et al, Chemical & Pharmaceutical Bulletin, 1964, 12(2), 182-191.*
Potts et al, JOC, 1988, 53, 2889-2898.*
Janz et al, JACS, 1955, 77, 3143-3145.*
Singer et al, JACS, 1935, 57, 1135-1137.*
Tolkmith et al, Science, 1967, 158(3807), 1462-1463.*
Khan et al, JCS, Section C, Organic, 1970, 1, 85-91.*
Ishikura et al, Chem. Pharm. Bull., 1985, 33(11), 4755-4763.*
Cherng, Y.J., Tetrahedron, 2002, 58, 887-890.*
Konishi et al, 1990, J. Pesticide, 15(1), 13-22.*
Japanese Abstract for Publication No. 54-117029 published Sep. 11, 1979, one page.
Japanese Abstract for Publication No. 54-147921 published Nov. 19, 1979, one page.
Japanese Abstract for Publication No. 62-000404 published Jan. 6, 1987, one page.
Partial English Translation of Japanese Patent Publication S42-19593 published Oct. 2, 1942, two pages.
International Preliminary Report on Patentability for corresponding PCT/JP2009/052077 mailed Sep. 16, 2010 six pages.
International Search Report for corresponding PCT/JP2009/052077 mailed Apr. 21, 2009, one page.
Supplementary European Search Report for corresponding Application No. 09707325.8 mailed Apr. 7, 2011, five pages.

* cited by examiner

*Primary Examiner* — Jeffrey S. Lundgren
*Assistant Examiner* — Ibrahim D Bori
(74) *Attorney, Agent, or Firm* — Rankin, Hill & Clark LLP

(57) ABSTRACT

The present invention provides a compound having an excellent inhibitory action on melanin production and being useful as a whitening agent, and a skin external preparation containing the compound. The whitening agent of the present invention comprises, as an active ingredient, a compound represented by formula (1) or a pharmacologically acceptable salt thereof:

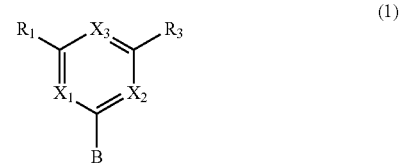

(1)

wherein $X_1$, $X_2$, and $X_3$ are each $CR_2$ or N; $R_1$, $R_2$, and $R_3$ are each H, $C_{1-6}$ alkyl, $C_{1-6}$ alkoxy, SH, OH, or $NR_bR_c$, wherein $R_b$ and $R_c$ are each H, $C_{1-6}$ alkyl, or hydroxy-$C_{1-6}$ alkyl, or $NR_bR_c$ forms a saturated or unsaturated 5- or 6-membered hetero ring; and B is a substituted or unsubstituted pyrazole, imidazole, pyridine, or piperidine; with the proviso that at least one of $R_1$, $R_3$, $R_4$, and $R_6$ is a group other than $C_{1-3}$ alkyl in the case where $X_1$=$X_2$=$Y_1$=N and $X_3$=$CR_2$.

2 Claims, No Drawings

WHITENING AGENT AND SKIN EXTERNAL PREPARATION

RELATED APPLICATIONS

This application claims, the priority of Japanese Patent Application No. 2008-29106 filed on Feb. 8, 2008 and Japanese Patent Application No. 2008-199606 filed on Aug. 1, 2008, which are incorporated herein by reference.

FIELD OF THE INVENTION

The present invention relates to a whitening agent and a skin external preparation, and particularly, to an active ingredient thereof.

BACKGROUND OF THE INVENTION

Pigmentation in the skin such as pigmented spots and freckles are resulted from hyperpigmentation of melanin in the epidermis. The hyperpigmentation is caused by acceleration of melanin production in epidermal melanocytes triggered by hormone abnormality or UV stimulation.

A whitening agent has been mixed into a skin external preparation with an aim to prevent and improve such abnormal melanin pigmentation. At present, as ingredients that are mixed into a skin external preparation as a whitening agent, there are vitamin C derivative, kojic acid, arbutin (4-hydroxyphenyl-β-D-glucopyranoside), Rucinol (4-n-butylresorcinol), ellagic acid, etc, which are known to have an inhibitory action on melanin production.

However, a whitening agent fully satisfactory in terms of the effect, safety, and the like has not yet been obtained, and therefore development of a new whitening agent has been demanded.

On the other hand, Patent Literature 1 describes a pyrazole pyrimidine compound having a regulatory action on a potassium channel.

Also, Patent Literatures 2 to 4 describe a pyrazole pyrimidine compound having a pest control activity on rice blast disease, leaf blight disease of rice and sesame, cucumber powdery mildew, and the like.

Further, Patent Literature 5 describes a pyrazole-pyrimidine compound useful as an analgesic.

However, these literatures are totally silent on an inhibitory action on melanin production and a whitening effect.

Patent Literature 1: WO2006/100212
Patent Literature 2: Japanese Unexamined Patent Publication No. S54-117029
Patent Literature 3: Japanese Unexamined Patent Publication No. S54-147921
Patent Literature 4: Japanese Unexamined Patent Publication No. S62-404
Patent Literature 5: Japanese Examined Patent Publication No. S42-19593

DISCLOSURE OF THE INVENTION

Problem to be Solved by the Invention

The present invention has been accomplished in view of the aforementioned problem of the conventional art. An object of the present invention is to provide a compound having an excellent inhibitory action on melanin production and being useful as a whitening agent, and a skin external preparation containing the compound.

Means to Solve the Problem

The present inventors conducted thorough research to solve the aforementioned problem. As a result, they have found that a specific compound has an excellent inhibitory action on melanin production and also has extremely low cytotoxicity, thereby completing the present invention.

That is, the whitening agent of the present invention comprises, as an active ingredient, a heterocyclic compound represented by formula (1) or a pharmacologically acceptable salt thereof:

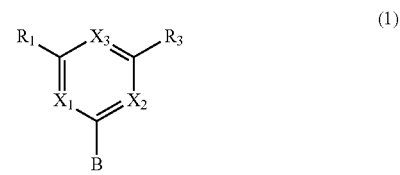

wherein
$X_1$, $X_2$, and $X_3$ are each independently $CR_2$ or N;
$R_1$, $R_2$, and $R_3$ are each independently H, $C_{1-6}$ alkyl, $C_{1-6}$ alkoxy, SH, OH, or $NR_bR_c$, wherein $R_b$ and $R_c$ are each independently H, $C_{1-6}$ alkyl, or hydroxy-$C_{1-6}$ alkyl, or $NR_bR_c$ forms a saturated or unsaturated 5- or 6-membered hetero ring;
B is a group represented by formula (B1) or (B2), wherein when $X_1$=$X_2$=$X_3$=$CR_2$, B is the group represented by the formula (B1):

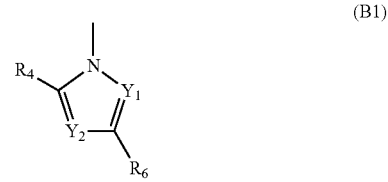

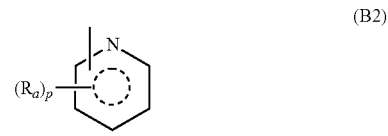

wherein
one of $Y_1$ and $Y_2$ is N, and the other is $CR_5$;
$R_4$, $R_5$, and $R_6$ are each independently H, $C_{1-6}$ alkyl, $C_{1-6}$ alkoxy, $C_{2-7}$ acyloxy, OH, amino, —NH-A, —NHCO-A, or —NHCOCH$_2$-A, wherein A is $C_{1-6}$ alkyl, phenyl, or a 5- or 6-membered heterocyclic group, or
$R_4$ and $R_5$, or $R_5$ and $R_6$ together form a 5- or 6-membered hydrocarbon ring condensed with the hetero ring to which $R_4$, $R_5$, and $R_6$ are bound;
the group (B2) is a saturated or unsaturated 6-membered heterocyclic group;
Ra is $C_{1-6}$ alkyl; and
p is an integer of 0 to 2, wherein when p is 2, Ra can be the same or different;
with the proviso that at least one of $R_1$, $R_3$, $R_4$, and $R_6$ is a group other than $C_{1-3}$ alkyl in the case where $X_1$=$X_2$=$Y_1$=N and $X_3$=$CR_2$.

The present invention also provides the whitening agent, wherein B is the group (B1).

The present invention also provides the whitening agent, wherein the active ingredient is a heterocyclic compound represented by formula (1-1) or a pharmacologically acceptable salt thereof:

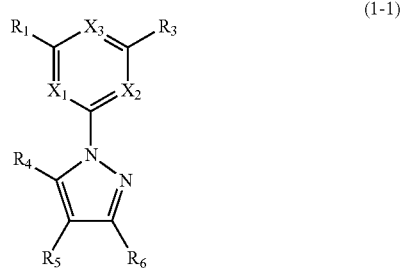

(1-1)

wherein, $X_1$, $X_2$, $X_3$, $R_1$, $R_3$, $R_4$, $R_5$, and $R_6$ are as defined in the formula (1).

The present invention also provides the whitening agent, wherein the active ingredient is a heterocyclic compound represented by formula (1-1a) or a pharmacologically acceptable salt thereof:

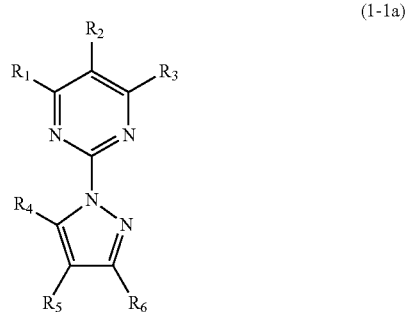

(1-1a)

wherein, $R_1$, $R_2$, $R_3$, $R_4$, $R_5$, and $R_6$ are as defined in the formula (1).

The present invention also provides the whitening agent, wherein $X_1=X_2=X_3=N$ in the formula (1-1).

The present invention also provides the whitening agent, wherein $X_1=X_2=X_3=CR_2$ in the formula (1-1).

The present invention also provides the whitening agent, wherein B is the group (B1), $X_1=X_2=N$, $X_3=CR_2$, and $Y_2=N$.

The present invention also provides the whitening agent, wherein B is the group (B1), and $R_1$ and $R_3$ are each independently H or $C_{1-6}$ alkyl.

The present invention also provides the whitening agent, wherein B is the group (B1), and at least one of $R_1$ and $R_3$ is $NR_bR_c$.

The present invention also provides the whitening agent, wherein B is the group (B1), at least one of $X_1$, $X_2$, and $X_3$ is $CR_2$, and $R_2$ is H or $C_{1-6}$ alkyl.

The present invention also provides the whitening agent, wherein B is the group (B1), and $R_5$ and $R_6$ are each independently H or $C_{1-6}$ alkyl.

The present invention also provides the whitening agent, wherein B is the group (B1), and $R_4$ is H, $C_{1-6}$ alkyl, $C_{1-6}$ alkoxy, $C_{2-7}$ acyloxy, OH, or amino.

The present invention also provides the whitening agent, wherein B is the group (B1), and $R_4$ is —NH-A, —NHCO-A, or —NHCOCH$_2$-A, or $R_4$ and $R_5$ together form the 5- or 6-membered hydrocarbon ring condensed with the hetero ring to which $R_4$ and $R_5$ are bound.

The present invention also provides the whitening agent, wherein at least one of $X_1$, $X_2$, and $X_3$ is N, and B is the group (B2).

The present invention also provides the whitening agent, wherein B is the group (B2), $X_1=X_2=N$, and $X_3=CR_2$.

The present invention also provides the whitening agent, wherein B is the group (B1), and $R_4$ is —NH-A, —NHCO-A, or —NHCOCH$_2$-A, or $R_4$ and $R_5$ together form the 5- or 6-membered hydrocarbon ring condensed with the hetero ring to which $R_4$ and $R_5$ are bound.

The present invention also provides the whitening agent, wherein at least one of $X_1$, $X_2$, and $X_3$ is N, and B is the group (B2).

The present invention also, provides the whitening agent, wherein B is the group (B2), $X_1=X_2=N$, and $X_3=CR_2$.

The present invention also provides the whitening agent, wherein the active ingredient is a heterocyclic compound represented by formula (1-2) or a pharmacologically acceptable salt thereof:

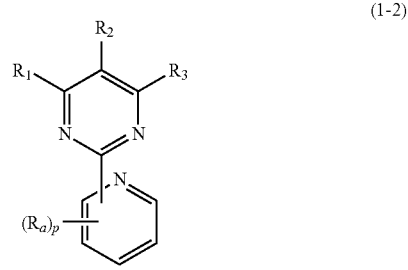

(1-2)

wherein $R_1$, $R_2$, $R_3$, Ra, and p are as defined in the formula (1).

The present invention also provides the whitening agent, wherein p in the formula (1-2) is 0.

The present invention also provides the whitening agent, wherein B is the group (B2) and $R_1$, $R_2$, and $R_3$ are each independently H, $C_{1-6}$ alkyl, $C_{1-6}$ alkoxy, or $NR_bR_c$.

The present invention also provides the whitening agent, wherein the active ingredient inhibits melanin production.

The present invention also, provides a skin external preparation and a cosmetic comprising any of the aforementioned heterocyclic compounds or a pharmacologically acceptable salt thereof.

Effect of the Invention

The whitening agent of the present invention has an excellent inhibitory action on melanin production and also has, extremely low cytotoxicity; therefore, it can be suitably mixed into a skin external preparation as a whitening agent.

BEST MODE FOR CARRYING OUT THE INVENTION

The whitening agent of the present invention comprises a compound represented by the following formula (I):

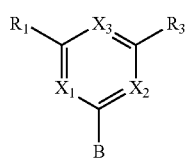

(1)

In the formula (1), $X_1$, $X_2$, and $X_3$ are each independently $CR_2$ or N. Accordingly, the unsaturated 6-membered ring containing $X_1$, $X_2$, and $X_3$ is a benzene ring, a pyridine ring, a pyrimidine ring, or a triazine ring. Among them, preferred examples include a benzene ring or an unsaturated 6-membered ring wherein $X_1=X_2=N$, and more preferred examples include a pyrimidine ring.

$R_1$, $R_2$, and $R_3$ are each independently H, $C_{1-6}$ alkyl, $C_{1-6}$ alkoxy, SH, OH, or a group represented by $NR_bR_c$. When a plurality of $R_2$ is present, the $R_2$ may be the same or different.

$R_b$ and $R_c$ are each independently H, $C_{1-6}$ alkyl, or hydroxy-$C_{1-6}$ alkyl. Alternatively, $R_b$ and $R_c$ of $NR_bR_c$ can form a saturated or unsaturated 5- or 6-membered hetero ring together with, the nitrogen atom to which $R_b$ and $R_c$ bound.

Examples of the saturated or unsaturated 5- or 6-membered hetero ring formed by $NR_bR_c$ include a hetero ring containing one to four hetero atoms (a N, O, or S atom) as ring-constituent elements, such as pyrrole, pyrroline, pyrrolidine, pyrazole, pyrazoline, pyrazolidine, imidazole, triazole, tetrazole, thiazolidine, piperidine, piperazine, oxazine, and morpholine. Among them, preferred examples include morpholine and pyrazole. Also, the hetero ring formed by $NR_bR_c$ may have one to three $C_{1-6}$ alkyl groups as substituents at any possible position.

When at least one of $X_1$, $X_2$, and $X_3$ is N, B is a group represented by the following formula (B1) or (B2); however, when $X_1=X_2=X_3=CR_2$ (benzene ring), B is the group represented by the formula (B1):

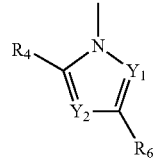

(B1)

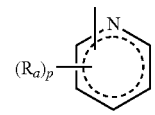

(B2)

In the group (B1), one of $Y_1$ and $Y_2$ is N, and the other is $CR_5$. Accordingly, the group (B1) is a pyrazol-1-yl group (in the case where $Y_1=N$) or an imidazol-1-yl group (in the case where $Y_2=N$).

$R_4$, $R_5$, and $R_6$ can be each independently selected from H, $C_{1-6}$ alkyl, $C_{1-6}$ alkoxy, $C_{2-7}$ acyloxy, OH, amino, —NH-A, —NHCO-A, or —NHCOCH$_2$-A (A is $C_{1-6}$ alkyl, phenyl, or a 05- or 6-membered heterocyclic group). Among them, $R_5$ and $R_6$ are each preferably H or $C_{1-6}$ alkyl. Alternatively, $R_4$ and $R_5$, or $R_5$ and $R_6$ together form a 5- or 6-membered hydrocarbon group ring condensed with the hetero ring to which $R_4$, $R_5$, and $R_6$ are bound.

However, in the present invention, at least one of $R_1$, $R_3$, $R_4$, and $R_6$ is a group other than $C_{1-3}$ alkyl when $X_1=X_2=Y_1=N$ and $X_3=CR_2$.

The 5- or 6-membered heterocyclic ring of A can be a saturated or unsaturated heterocyclic group containing one to four hetero atoms (a N, O, or S atom). Examples thereof include furan, tetrahydrofuran, dioxofuran, thiophene, tetrahydrothiophene, pyrrole, pyrroline, pyrrolidine, pyrazole, pyrazoline, pyrazolidine, imidazole, triazole, tetrazole, isoxazole, oxazole, oxazoline, oxadiazole, isothiazole, thiazole, thiazoline, thiazolidine, pyran, tetrahydropyran, dioxane, dioxin, thiane, oxathiane, dithiane, pyridine, piperidine, pyridazine, pyrimidine, pyrazine, piperazine, triazine, tetrazine, oxazine, morpholine, and thiazine, Preferred examples of the hetero ring of A include thiophene and piperazine.

It is to be noted that the phenyl and the heterocyclic group of A may have one to three substituents at any possible position. Examples of such a substituent include, in addition to $C_{1-6}$ alkyl, a halogen (Br, Cl, or I), and $C_{1-6}$ alkoxycarbonyl, $C_{1-2}$ alkylenedioxy such as methylenedioxy (—OCH$_2$O—) and ethylenedioxy (—OCH$_2$CH$_2$O—).

Further, the 5- or 6-membered hydrocarbon ring formed by $R_4$ and $R_5$, or $R_5$ and $R_6$, which is condensed with the hetero ring to which $R_4$, $R_5$, and $R_6$ are bound, may have one or two substituents at any possible position. Examples of such a substituent include a benzylidene group that may be substituted by one or two halogens.

Among the compounds represented by the formula (1), a preferred example of the compound wherein B=the group (B1) is a pyrazole compound represented by the following formula (1-1):

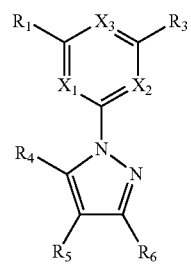

(1-1)

In the formula (1-1), $X_1$, $X_2$, $X_3$, $R_1$, $R_3$, $R_4$, $R_5$, and $R_6$ are as defined in the formula (1).

It is to be noted that the compounds of formula (1-1) wherein $R_4$=OH can be tautomers as shown below. In the present invention, such tautomers are also included in the compounds of the formula (1-1).

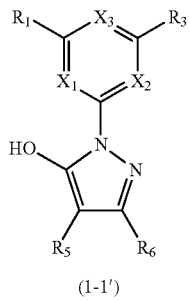

(1-1')

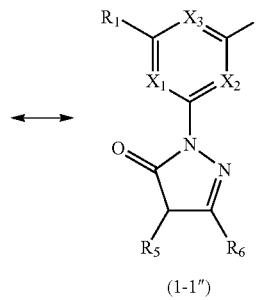

(1-1'')

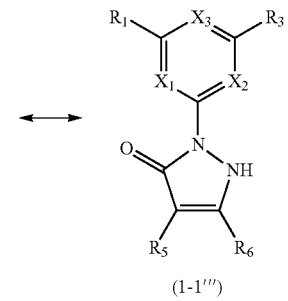

(1-1''')

A preferred example of the compound represented by the formula (1-1) is a pyrazole compound represented by the following formula (1-1a):

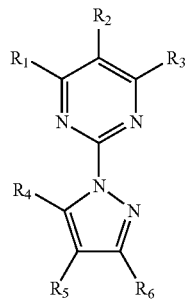

(1-1a)

In the formula (1-1a), $R_1$, $R_2$, $R_3$, $R_4$, $R_5$, and $R_6$ are as defined in the formula (1).

Another preferred example of the compound represented by the formula (1-1) is a pyrazole compound wherein $X_1=X_2=X_3=N$.

Another preferred example of the compound represented by the formula (1-1) is a pyrazole compound wherein $X_1=X_2=X_3=CR_2$.

A preferred example of the compound wherein B=the group (B1) is an imidazole compound wherein $X_1=X_2=N$, $X_3=CR_2$, and $Y_2=N$.

Another preferred example of the compound wherein B=the group (B1) is a compound wherein $R_1$ and $R_3$ are each independently H or $C_{1-6}$ alkyl.

Another preferred example of the compound wherein B=the group (B1) is a compound wherein at least one of $R_1$ and $R_3$ is $NR_bR_c$.

Another preferred example of the compound wherein B=the group (B1) is a compound wherein at least one of $X_1$, $X_2$, and $X_3$ is $CR_2$, and $R_2$ is H or $C_{1-6}$ alkyl.

When at least one of $X_1$, $X_2$, and $X_3$ in the formula (1) is N, B can be the group (B2). The group (B2) is a saturated or unsaturated 6-membered heterocyclic group, and thus, the heterocyclic ring is piperidine or pyridine.

Ra is $C_{1-6}$ alkyl.

p is an integer of 0 to 2, and when p is 2, Ra can be the same or different.

Among the compounds represented by the formula (1), a preferred example of the compound wherein B=the group (B2) is a compound wherein $X_1=X_2=N$ and $X_3=CR_2$. A preferred example thereof is a pyrimidine compound represented by the following formula (1-2):

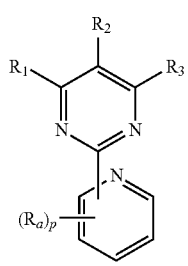

(1-2)

In the formula (1-2), $R_1$, $R_2$, $R_3$, $R_a$, and p are as defined in the formula (1).

A preferred example of the compound represented by the formula (1-2) is a compound wherein p is zero.

Also, a preferred example of the compound wherein B=the group (B2) is a compound wherein $R_1$, $R_2$, and $R_3$ are each independently H, $C_{1-6}$ alkyl, $C_{1-6}$ alkoxy, or $NR_bR_c$.

It is to be noted that, in the present invention, each group is defined as follows.

The "$C_{1-6}$ alkyl" is a linear, branched, or cyclic saturated hydrocarbon group having 1 to 6 carbon atoms. Examples thereof include a methyl group, an ethyl group, an n-propyl group, an isopropyl group, an n-butyl group, an isobutyl group, a sec-butyl group, a tert-butyl group, an n-pentyl group, an isoamyl group, an n-hexyl group, an n-octyl group, a cyclopropyl group, a cyclobutyl group, a cyclopentyl group, and a cyclohexyl group. Preferred alkyl includes methyl and ethyl.

The "$C_{1-6}$ alkoxy" is an oxy group having a $C_{1-6}$ alkyl group.

The "hydroxy-$C_{1-6}$ alkyl" is $C_{1-6}$ alkyl having one or two hydroxyl groups at any possible position.

The "$C_{2-7}$ acyl" represents a carbonyl group having $C_{1-6}$ alkyl or phenyl. Examples thereof include an acetyl group, a propionyl group, a butyryl group, an acryloyl group, a butenoyl group, and a benzoyl group. Preferred acyl includes an acetyl group.

The compound of the formula (1) can be synthesized by a known method or commercially available. Hereinbelow, representative synthesis examples are described; however, the present invention is not limited thereto. When the molecule has a functional group which blocks or might block a reaction, an appropriate protecting group is preferably used to allow the reaction to proceed efficiently. The use of the protecting group can be carried out according to, for example, Protective Groups in Organic Synthesis by Theodora W. Greene and Peter G. M. Wuts.

Further, when an isomer such as a conformational isomer, a geometric isomer, and an optical isomer is present, a pure isomer or geometric isomer can be obtained by appropriately selecting a raw material and a reaction condition and performing a separation operation. In the present invention, a pure isomer of the compound of the formula (1) as well as a mixture thereof are also included.

Among the compounds of the formula (1), for example, a compound represented by the formula (1-1) can be obtained by a reaction shown in the following scheme 1.

Scheme 1:

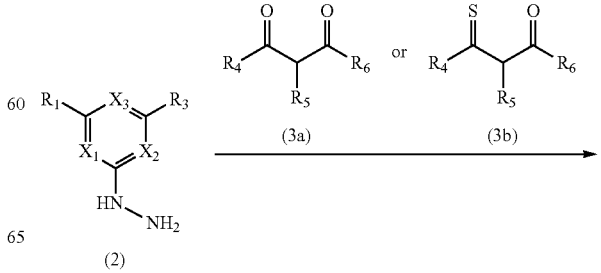

-continued

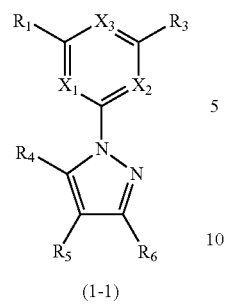

(1-1)

-continued

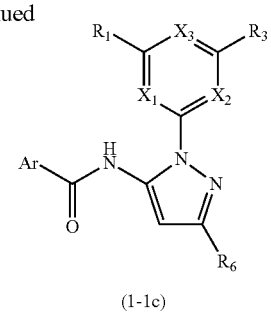

(1-1c)

In scheme 1, a reaction of a hydrazine compound (2) with a 1,3-dicarbonyl compound (3a) or a 1-sulfonyl-3-carbonyl compound (3b) can be carried out, for example, in an appropriate solvent such as methanol in the presence of an acid catalyst such as hydrochloric acid or acetic acid, while heating as needed. This reaction can be carried out according to, for example, a method described in Japanese Unexamined Patent Publication No. S62-404 (Patent Literature 4), Tetrahedron Lett., 45, 4265 (2004), Gazzetta Chemica Italiana, 93, 100 (1963), or the like.

Among the compounds represented by the formula (1-1), a compound (1-1b) wherein $R_4$ is —$NH_2$ can be obtained by a reaction with a compound (4) or compound (5) as shown in the following scheme 2. Further, by reacting the compound (1-1b) with a halogenated acyl compound (7), a compound (1-1c) wherein $R_4$ is —NHCO-Ar (Ar: aryl) can be derived. These reactions can be carried out according to a method described in J. Chem. Soc., 285 (1941), Japanese Unexamined Patent Publication No. H4-275227, Japanese Unexamined Patent Publication No. 2006-526015, and the like.

Scheme 2:

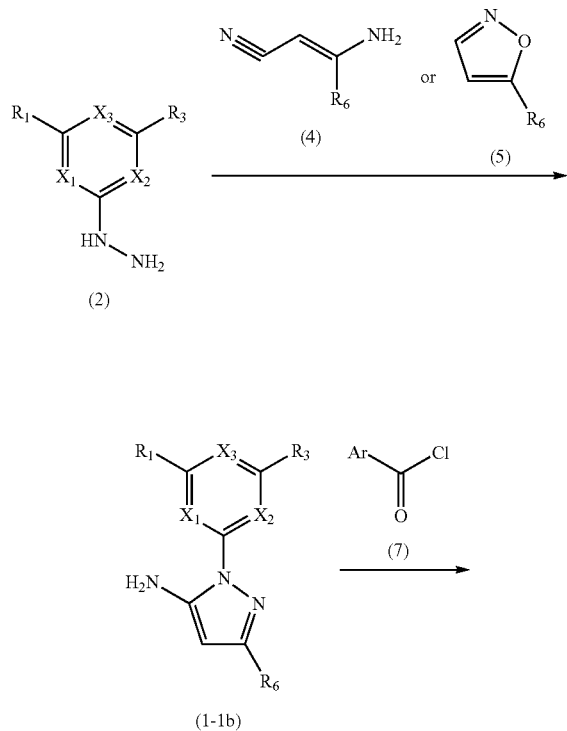

The hydrazine compound (2) to be used as a starting material in the schemes 1 and 2 can be commercially available or synthesized by a known method.

For example, by a reaction shown in the following scheme 3 using an amine compound (8) as a starting material, the objective hydrazine compound (2) can be obtained. This reaction can be carried out according to a method described in Japanese. Unexamined Patent Publication No. H8-208620.

Scheme 3:

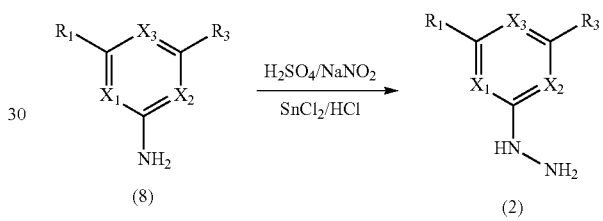

Alternatively, by a reaction shown in the following scheme 4, the objective hydrazine compound (2) can be obtained from a pyrimidine compound (9) having a leaving group Z (for example, a halogen). This reaction can be carried out according to, for example, a method described in Chem. Pharm. Bull., 17(7), 1467 (1969), Chem. Pharm. Bull., 11 (11), 1382 (1963), Yakugaku Zasshi, 73, 635 (1953), or the like.

Scheme 4:

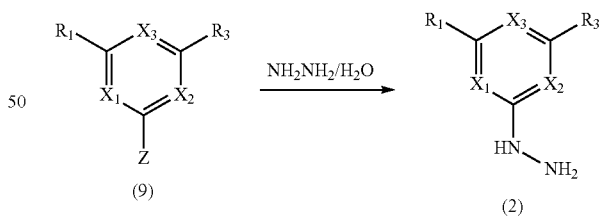

Other compounds used, in the aforementioned reactions can be synthesized by appropriately combining known methods.

The compound of the formula (1) can be converted into an acid-addition salt by an ordinary method as needed. Examples of acid in the acid-addition salt include an inorganic salt such as hydrochloric acid, hydrobromic acid, sulfuric acid, and phosphoric acid, and an organic acid such as acetic acid, propionic acid, citric acid, lactic acid, oxalic acid, maleic acid, fumaric acid, succinic acid, tartaric acid, and methanesulfonic acid.

Many of the compounds of the formula (1) are commercially available and can be obtained from various suppliers such as Enamine Ltd. (Ukraine), Pharmeks Ltd. (Russia), Labotest (Germany), Scientific Exchange Inc. (U.S.A), Life Chemicals Inc. (Ukraine), Asinex Ltd. (Russia), Vitas-M Laboratory Ltd. (Russia), ACB Blocks Ltd. (Russia), Bionet (U.S.A), and Princeton Biomolecular Research Inc. (U.S.A).

The compound of the formula (1) has an excellent inhibitory action on melanin production while exhibiting extremely low cytotoxicity. Therefore, the present compound is useful as a whitening agent and can be suitably mixed into various skin external preparations, particularly a skin external preparation intended to improve or prevent pigmented spots, freckles, skin dullness, and the like.

When the compound of the formula (1) is mixed into the skin external preparation as the whitening agent, the compound amount is, in the total amount of the external agent, typically 0.0002% by mass or more, preferably 0.002% by mass or more. When it is too low, the effect cannot be fully exerted. Although no limitation is imposed on the upper limit, it is typically 30% by mass or less, preferably 20% by mass or less, and more preferably 5% by mass or less. When the compound is excessively mixed in, not only a remarkable effect reasonably expected from the increased amount may not be obtained but also formulation designing and usability may be affected.

Other than adding the compound of the formula (1), the skin external preparation of the present invention can be produced by an ordinary method.

In addition to the compound of the formula (1), other ingredients normally used in a skin external preparation such as a cosmetic product and a pharmaceutical product can be appropriately added to the skin external preparation of the present invention as needed as far as the effect of the present invention is not adversely affected. Examples of such an ingredient include oil, a humectant, an ultraviolet protective agent, an antioxidant, a metal ion chelating agent, a surfactant, a preservative, a moisturizer, a fragrance, water, an alcohol, a thickener, powder, a colorant, a crude drug, and various kinds of medicinal ingredients.

Further, other whitening agents such as vitamin C, magnesium ascorbyl phosphate, ascorbyl glucoside, arbutin, kojic acid, Rucinol, ellagic acid, tranexamic acid, and linoleic acid can be appropriately added.

The skin external preparation of the present invention is widely applicable to the fields of cosmetics, drugs, and quasi drugs. No particular limitation is imposed on the form of the skin external preparation as long as it is applicable to the skin. Any form such as a solution, an emulsion, a solid, a semi-solid, a powder, a powder dispersion, a water-oil-separated two-phase liquid, a water-oil-powder-separated three-phase liquid, an ointment, a gel, an aerosol, a mousse, and a stick can be applied. Further, the skin external preparation can be provided in any use form including a facial cosmetic such as a lotion, an emulsion, a cream, a pack, an essence, and a gel, and a makeup cosmetic such as a foundation, a makeup base, and a concealer.

Hereinbelow, the present invention will be further described with specific examples. However, the present invention is not limited thereto.

EXAMPLES

A test for melanin production inhibition by the compounds of the formula (1) was conducted. The test method is as follows.

Melanin Production Inhibition Test (1) Inoculation of Cells and Addition of Test Substances Mouse B16 melanoma cells were inoculated in a six well plate at 100,000 cells/well. The next day, test substance solutions (solvent: DMSO) were added.

(2) Cell Proliferation Test

Three days after the addition of the test substance solution, the medium was removed by aspiration. Then 1 ml of EMEM medium containing 10% Alamar Blue solution was added, and a reaction was allowed to proceed at 37° C. After 30 minutes, 100 µL of the reaction mixture was transferred to a 96 well plate and fluorescence was measured at an excitation wavelength of 544 nm and a measurement wavelength of 590 nm. Using the value thus measured as a relative value of cell count, a ratio of the cell count (% cell count) of the test substance-added group to the test substance-absent group (group in which only the solvent was added) was calculated. The higher the % cell count, the lower the cytotoxicity. It was determined that a compound having the % cell count of 80% or more was non-cytotoxic, and that a compound having the % cell count of less than 80% was cytotoxic.

(3) Quantification of Melanin

The cells after the cell proliferation test were washed with PBS three times, and then lysed by addition of 200 µL of 1M NaOH to measure an absorbance at 475 nm. Using the value thus measured as a: value of the melanin amount, a ratio of the melanin amount (%) of the test substance-added group to the test substance-absent group (group in which only the solvent was added) was calculated. The lower the ratio of the melanin amount, the higher the melanin production-inhibitory effect. In the final concentrations of the test substances at which the compound was determined to be non-cytotoxic, the minimum final concentration of the test substance at which the ratio of the melanin amount (%) was 80% or less was provided as a minimum concentration for inhibition of melanin production (ppm). The inhibitory effect on melanin production was evaluated according to the following criteria.

◉: the minimum concentration for inhibition of melanin production was 1 ppm or less.

○: the minimum concentration for inhibition of melanin production was more than 1 ppm and 10 ppm or less.

×: no inhibitory effect on melanin production was exhibited at 10 ppm or less (the ratio of the melanin amount was not 80% or less even at 10 ppm or less).

The results of melanin production inhibition test using the compounds of the present invention are shown in Tables 1 to 5. The test substances shown in each table are either sold on the open market or synthesized according to Synthesis Examples described later.

Any of the compounds shown in Tables 1 to 5 was acknowledged to have an inhibitory effect on melanin production, and most of them exhibited the effect at such an extremely low concentration as 1 ppm or less.

It is to be noted that symbols in Tables represent the following groups.

Me: Methyl, Et: Ethyl, iPr: Isopropyl, CycHex: Cyclohexyl, Ac: Acetyl

TABLE 1

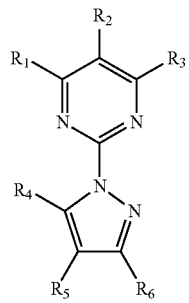

| No. | R¹ | R² | R³ | R⁴ | R⁵ | R⁶ | Inhibitory effect on melanin production |
|---|---|---|---|---|---|---|---|
| 1 | Me | H | Me | NH₂ | H | Me | ◉ |
| 2 | Me | H | Morpholino | Me | H | Me | ◉ |
| 3 | H | H | H | NH₂ | H | Me | ○ |
| 4 | H | H | H | Me | H | Me | ◉ |
| 5 | Me | H | O—Me | O—Me | H | Me | ◉ |
| 6 | Me | H | SH | Me | H | Me | ◉ |
| 7 | Me | H | NHMe | Me | H | Me | ◉ |
| 8 | Me | H | Me | OH | Et | Me | ◉ |
| 9 | Me | H | Me | O—Ac | Et | Me | ◉ |
| 10 | Me | H | O—Me | Me | H | Me | ◉ |
| 11 | Me | H | Me | OH | H | Me | ○ |
| 12 | Me | H | Me | H | H | H | ○ |

TABLE 1-continued

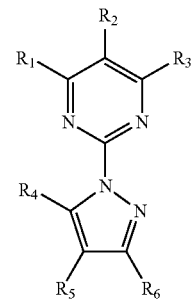

| No. | R¹ | R² | R³ | R⁴ | R⁵ | R⁶ | Inhibitory effect on melanin production |
|---|---|---|---|---|---|---|---|
| 13 | O—Me | H | O—Me | Me | H | Me | ◉ |
| 14 | Me | H | N—Me² | Me | H | Me | ◉ |
| 15 | Me | H | NHC₂H₄OH | Me | H | Me | ◉ |
| 16 | Me | H | NH—CycHex | Me | H | Me | ◉ |
| 17 | Me | H | Me | Me | H | H | ◉ |
| 18 | Me | H | Me | H | H | Me | ◉ |
| 19 | Me | H | 3,5-Dimethyl pyrazol-1-yl | Me | H | Me | ◉ |
| 20 | Me | H | morpholino | Me | Me | Me | ◉ |
| 21 | H | Et | H | Me | H | Me | ◉ |
| 22 | H | H | Me | Me | H | Me | ◉ |
| 23 | Me | H | Me | H | Me | H | ◉ |

TABLE 2

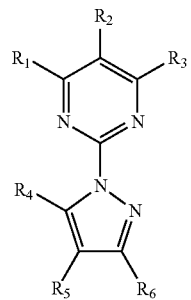

| No. | R¹ | R² | R³ | R⁵ | R⁶ | R⁴ | Inhibitory effect on melanin production |
|---|---|---|---|---|---|---|---|
| 24 | Me | H | Me | H | Me | —NHCO—IPr | ◉ |
| 25 | Me | H | Me | H | Me | —NH-(4-methylphenyl) | ◉ |
| 26 | Me | H | Me | H | Me | —NHCO-(4-chlorophenyl) | ◉ |
| 27 | Me | H | Me | H | Me | —NHCO-(3,4-methylenedioxyphenyl) | ◉ |
| 28 | Me | H | Me | H | Me | —NHCO-(2-methylthiophene-5-yl) | ◉ |
| 29 | Me | H | Me | H | Me | —NHCOCH2-(4-ethoxycarbonyl piperazin-1-yl) | ◉ |
| 30 | | | | | | 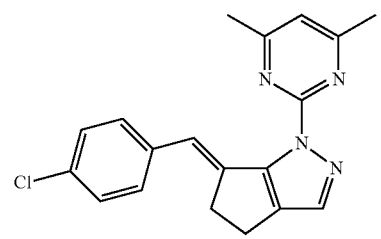 | ◉ |

TABLE 3

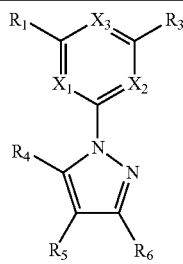

| No. | X³ | X¹ | X² | R¹ | R³ | R⁴ | R⁵ | R⁶ | Inhibitory effect on melanin production |
|---|---|---|---|---|---|---|---|---|---|
| 31 | CH | CH | N | H | H | NH² | H | Me | ○ |
| 32 | CH | CH | CH | Me | Me | NH² | H | Me | ◉ |
| 33 | CH | CH | CH | H | H | Me | H | Me | ○ |
| 34 | CMe | CH | CH | H | Me | Me | H | Me | ◉ |
| 35 | CH | CH | CH | Me | Me | Me | H | Me | ◉ |
| 36 | CH | CH | CH | H | Me | Me | H | Me | ◉ |
| 37 | N | CH | N | Me | NH² | Me | H | Me | ○ |
| 38 | N | N | N | Morpholino | Morpholino | Me | H | Me | ◉ |
| 39 | N | N | N | N—Me² | N—Me² | Me | H | Me | ◉ |
| 40 | CH | CH | N | Me | H | Me | H | Me | ○ |

TABLE 4

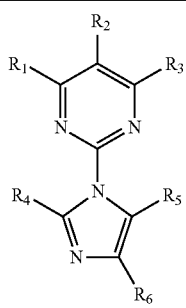

| No. | R¹ | R² | R³ | R⁴ | R⁵ | R⁶ | Inhibitory effect on melanin production |
|---|---|---|---|---|---|---|---|
| 41 | Me | H | Me | Me | H | H | ◉ |
| 42 | Me | H | Me | H | H | Me | ◉ |

TABLE 5

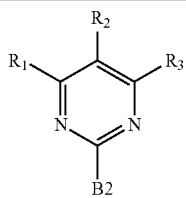

| No. | R¹ | R² | R³ | B2 | Inhibitory effect on melanin production |
|---|---|---|---|---|---|
| 43 | H | O—Me | O—Me | 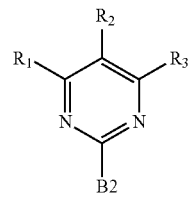 | ◉ |

TABLE 5-continued

| No. | R¹ | R² | R³ | B2 | Inhibitory effect on melanin production |
|---|---|---|---|---|---|
| 44 | H | O—Me | N—Me² | 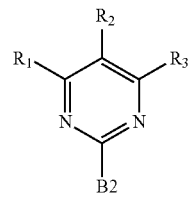 | ◉ |
| 45 | Me | H | Me | 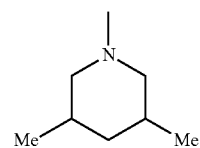 | ○ |

The minimum concentrations at which an inhibitory effect on melanin production was significantly exhibited in melanoma B16 cells were compared between the heterocyclic compounds of the present invention and arbutin, which is actually used in clinical practice within a range of 0.1 to 30% by mass in a composition. As representative examples, results of Compounds 7 and 14 are shown.

TABLE 6

| Test compound | Minimum concentration (%) |
|---|---|
| Arbutin | $5 \times 10^{-4}$ |
| Compound 7 | $3 \times 10^{-6}$ |
| Compound 14 | $3 \times 10^{-6}$ |

As shown in Table 6 above, the compounds of the present invention exhibited an inhibitory effect on melanin production in melanoma B16 cells at a concentration of approximately 1/170 of arbutin. Thus, it is understood that the compounds of the present invention exhibit the effect at a very low concentration compared to arbutin.

Hereinbelow, representative synthesis examples of the heterocyclic compounds used for the whitening agent of the present invention will be shown. Various heterocyclic compounds can be obtained by carrying out a reaction according to the below-described synthesis examples using a corresponding raw material.

Synthesis Example 1-1

Synthesis of 1-phenyl-3,5-dimethylpyrazole (Compound 33)

In a 100 mL recovery flask, phenylhydrazine (1.00 g, 9.25 mmol), acetylacetone (0.93 g, 9.25 mmol), ion-exchanged water (3.0 mL) and acetic acid (3.0 mL) were added and refluxed for one hour. Upon completion of the reaction, a 10% aqueous solution of sodium hydroxide was added to the reaction mixture to adjust the pH to 10 or higher. The mixture was extracted with ethyl acetate, and the organic phase was washed with saturated brine once and dried over anhydrous magnesium sulfate. The solvent was distilled off under reduced pressure, and the residue was purified by silica gel column chromatography (hexane:ethyl acetate=10:1) to give 1.56 g of 1-phenyl-3,5-dimethylpyrazole (Compound 33) (yield 98%).

Synthesis Example 1-2

Synthesis of (hetero)arylpyrazoles

In the same manner as in Synthesis Example 1-1 except that raw material A and raw material B were used instead of phenylhydrazine and acetylacetone, respectively, (hetero)arylpyrazoles as shown in Tables 7 and 8 were each synthesized.

TABLE 7

| No. | Strucure | Raw material A | Raw material B | NMR | Yield |
|---|---|---|---|---|---|
| 33 | | Phenylhydrazine | Acetylacetone | $^1$H-NMR (DMSO-d6): 218 (3H, s), 2.28 (3H, s), 6.05 (1H, s), 7.33-7.40 (1H, m), 7.45-7.52 (4H, m) | 98% |
| 46 | | Phenylhydrazine | 3-Aminocrotononitrilo | $^1$H-NMR (DMSO-d6): 2.06 (3H, s), 5.15 (2H, br-s), 5.32 (1H, s), 7.23-7.28 (1H, m), 7.40-7.46 (2H, m), 7.53-7.57 (2H, m) | 68% |
| 1 | | (4,6-Dimethylpyrimidin-2-yl)hydrazine | 3-Aminocrotononitrile | $^1$H-NMR (DMSO-d6): 2.07 (3H, s), 2.44 (6H, s), 5.24 (1H, s), 6.64 (2H, br-s), 7.04 (1H, s) | 68% |

TABLE 7-continued

| No. | Strucure | Raw material A | Raw material B | NMR | Yield |
|-----|----------|----------------|----------------|-----|-------|
| 34 | 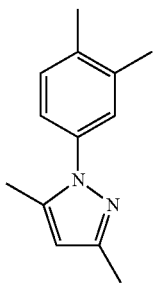 | (3,4-Dimethylphenyl)-hydrazine | Acetylacetone | $^1$H-NMR (CDCl$_3$): 2.24 (3H, s), 2.27 (3H, s), 2.27 (3H, s), 2.28 (3H, s), 5.96 (1H, s), 7.08-7.27 (3H, m) | 88% |
| 35 | 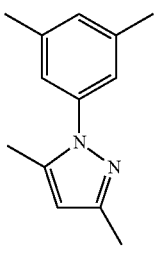 | (3,5-Dimethylphenyl)-hydrazine | Acetylacetone | $^1$H-NMR (DMSO-d6): 2.16 (3H, S), 2.26 (3H, s), 2.32 (6H, s), 6.02 (1H, s), 6.99 (1H, s), 7.07 (2H, s) | 94% |
| 36 | 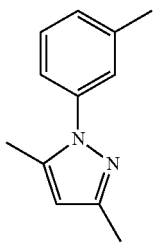 | 3-Methylphenylhydrazine | Acetylacetone | $^1$H-NMR (CDCl$_3$): 2.29 (3H, s), 2.29 (3H, s), 2.40 (3H, s), 5.98 (1H, s), 7.13-7.20 (2H, m), 7.25-7.34 (2H, m) | 98% |
| 20 | 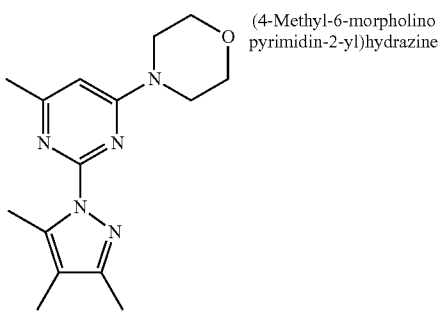 | (4-Methyl-6-morpholino pyrimidin-2-yl)hydrazine | 3-Methyl-2,4-pentanedione | $^1$H-NMR (CDCl$_3$) : 1.95 (3H, s), 2.27 (3H, s), 2.47 (3H, s), 2.61 (3H, s), 3.62-3.65 (4H, m), 3.78-3.81 (4H, m), 6.21 (1H, s) | 52% |

TABLE 8

| No. | Structure | Raw material A | Raw material B | NMR | Yield |
|-----|-----------|----------------|----------------|-----|-------|
| 17 | 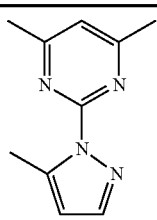 | (4,6-Dimethylpyrimidin-2-yl)hydrazine | 1,1-Dimethoxy-3-butanone | $^1$H-NMR (CDCl$_3$): 2.55 (6H, s), 2.70 (3H, s), 6.20 (1H, d), 6.93 (1H, s), 7.65 (1H, d) | 40% |

TABLE 8-continued

| No. | Structure | Raw material A | Raw material B | NMR | Yield |
|---|---|---|---|---|---|
| 18 | 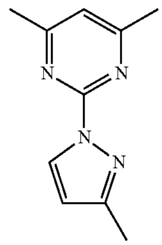 | (4,6-Dimethylpyrimidin-2-yl)hydrazine | 1,1-Dimethoxy-3-butanone | $^1$H-NMR (CDCl$_3$); 2.42 (3H, s), 2.53 (6H, s), 6.26 (1H, d), 6.87 (1H, s), 8.52 (1H, d) | 34% |
| 11 | 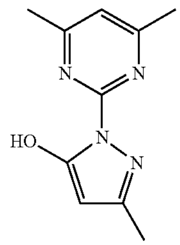 | (4,6-Dimethylpyrimidin-2-yl)hydrazine | Methyl acetoacetate | $^1$H-NMR (DMSO-d6): 2.14 (3H, s), 2.48 (6H, s), 5.48 (1H, s), 7.17 (1H, s), 12.24 (1H, s) | 23% |
| 13 | 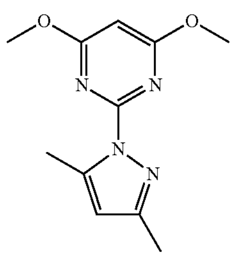 | (4,6-Dimetboxypyrimidin-2-yl)hydrazine | Acetylacetone | $^1$H-NMR (CDCl$_3$): 2.33 (3H, s), 2.68 (3H, s), 4.02 (6H, s), 5.91 (1H, s), 6.02 (1H, s) | 62% |
| 4 | 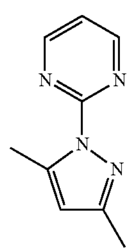 | 2-Hydrazinopyrimidine | Acetyl acetone | $^1$H-NMR (DMSO-d6): 2.20 (3H, s), 2.55 (3H, s), 6.14 (1H, s), 7.42 (1H, t), 8.85 (2H, d) | 94% |
| 3 | 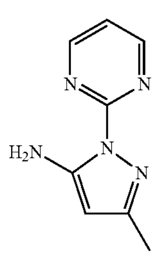 | 2-Hydrazinopyrimidine | 3-Aminocrotononitrile (CH$_3$C(NH$_2$)=CHCN) | $^1$H-NMR (DMSO-d6): 2.07 (3H, s), 5.26 (1H, s), 6.63 (2H, br-s), 7.29 (1H, t), 8.76 (2H, d) | 48% |

Synthesis Example 2

Synthesis of 2-(pyrazol-1-yl)-4,6-dimethylpyrimidine (Compound 12)

In a 100 mL recovery flask, 1-amidinopyrazole hydrochloride (1.00 g, 6.82 mmol), acetylacetone (0.72 g, 7.16 mmol), and methanol (6.82 mL) were added. 2N hydrochloric acid (3.0 mL) was added dropwise to the mixture at room temperature, and the refluxed for five hours. Upon completion of the reaction, a 10% aqueous solution of sodium hydroxide was added to the reaction mixture to adjust the pH of 10 or higher. The mixture was extracted with ethyl acetate twice, and the organic phase was washed with saturated brine once and dried over anhydrous magnesium sulfate. The solvent was distilled off under reduced pressure and the residue was purified by silica gel column chromatography (chloroform) to give 0.08 g of 2-(pyrazol-1-yl)-4,6-dimethylpyrimidine (Compound 12) (yield 7%).

$^1$H-NMR (CDCl$_3$): 2.55 (6H, s), 6.47 (1H, dd), 6.93 (1H, s), 7.81 (1H, d), 8.62 (1H, d).

Synthesis Example 3-1

Synthesis of 1-(5-ethylpyrimidin-2-yl)-3,5-dimethylpyrazole (Compound 21)

5-Ethyl-2-hydrazinopyrimidine (400 mg, 2.89 mmol) was suspended in 3 mL of water, and acetylacetone (314 μL, 3.04 mmol) and 2 mol/L hydrochloric acid (330 μL) were added thereto and stirred at room temperature for 23 hours. 2 mL of sodium hydroxide aqueous solution was added to the reaction mixture to adjust the pH to 12. The mixture was extracted with ethyl acetate three times, and the organic phase was washed with saturated brine, dried over anhydrous sodium sulfate, and then filtrated. The filtrate was concentrated under reduced pressure, and the residue was purified by silica gel column chromatography (hexane:ethyl acetate=90:10→10:90) and silica gel column chromatography (methylene chloride:methanol=100:0→95:5) to give 203 mg of the title compound (yield 35%).
$^1$H-NMR (CDCl$_3$): 1.30 (3H, s), 2.34 (3H, s). 2.64 (3H, s), 2.64-2.70 (2H, m), 6.03 (1H, s), 8.57 (2H, s).

Synthesis Example 3-2

Synthesis of 1-(4-methylpyrimidin-2-yl)-3,5-dimethylpyrazole (Compound 22)

In a similar manner to Synthesis Example 3-1 except that 4-methyl-2-hydrazinopyrimidine was used instead of 5-ethyl-2-hydrazinopyrimidine, the title compound was obtained (yield 37%).
$^1$H-NMR (CDCl$_3$): 2.34 (3H, s), 2.59 (3H, s), 2.66 (3H, s), 6.03 (1H, s), 7.00 (1H, d), 8.57 (1H, d).

Synthesis Example 4

Synthesis of 1-(4-methylpyridin-2-yl)-3,5-dimethylpyrazole (Compound 40)

(1) Synthesis of 2-hydrazino-4-methylpyridine hydrochloride

In a 25 mL recovery flask, hydrazine hydrate (5 g) was added, and then 2-chloro-4-methylpyridine (1.0 g, 7.84 mmol) was slowly added thereto at room temperature while stirring. After refluxing for three hours, the reaction mixture was cooled and extracted with chloroform twice. The organic phase was washed with saturated brine once and dried over, anhydrous magnesium sulfate. Then, the solvent was distilled off to give 2-hydrazino-4-methylpyridine (crude product).
The crude product thus obtained was dissolved in methanol (2 mL), and 3 mL of 4N hydrochloride solution in dioxane was added thereto while stirring with cooling at 0° C. The solid precipitated out after stirring for 30 minutes at 0° C. was collected by filtration and crystallized from a mixed solvent of methanol, chloroform, and hexane to give 0.55 g of 2-hydrazino-4-methylpyridine hydrochloride (yield 44%).

(2) Synthesis of 1-(4-methylpyridin-2-yl)-3,5-dimethylpyrazole

In a 50 mL recovery flask, 2-hydrazino-4-methylpyridine hydrochloride (0.5 g, 3.13 mmol), acetylacetone (0.376 g, 3.76 mmol), and water (7 mL) were added and stirred at room temperature for 16 hours. Upon completion of the reaction, a 10% aqueous solution of sodium hydroxide was added to the reaction mixture to adjust the pH up to 14. The resulting mixture was extracted with ethyl acetate twice, and the organic phases were combined and washed with saturated brine once, and then dried over anhydrous magnesium sulfate. Then, the solvent was distilled off under reduced pressure, and the residue was purified by silica gel column chromatography (hexane:ethyl acetate=4:1) to give 0.47 g of the title compound (yield 80%).
$^1$H-NMR (CDCl$_3$): 2.30 (3H, s), 2.40 (3H, s), 2.61 (3H, s), 5.98 (1H, s), 6.97 (1H, d), 7.66 (1H, s), 8.27 (1H, d).

Synthesis Example 5-1

Synthesis of 1-(pyrimidin-2-yl)-3,5-dimethylpyrazole (Compound 4)

NaH (0.594 g, 14.84 mmol) was suspended in THF (10 mL), and 3,5-dimethylpyrazole (1.091 g, 11.35 mmol) was slowly added and stirred for one hour at room temperature. 2-Chloropyrimidine (1 g, 8.73 mmol) was slowly added to the mixture and refluxed for three hours. Completion of the reaction was confirmed by TLC, and then water (5 mL) was added to the mixture. The solvent was distilled off and the residue was extracted with ethyl acetate twice. The organic phase was washed with saturated brine and dried over magnesium sulfate. The solvent was then distilled off and the residue was purified by silica gel column chromatography (hexane:ethyl acetate=1:2→ethyl acetate) to give 1.05 g of the title compound (yield 69%).

Synthesis Example 5-2

Synthesis of heteroarylpyrimidines

In the same manner as Synthesis Example 5-1 except that raw material A and raw material B were used instead of 2-chloropyrimidine and 3,5-dimethylpyrazole, respectively, heteroarylpyrimidines as shown in Table 9 were each synthesized.

TABLE 9

| No. | Structure | Raw material A | Raw material B | NMR | Yield |
|---|---|---|---|---|---|
| 2 | 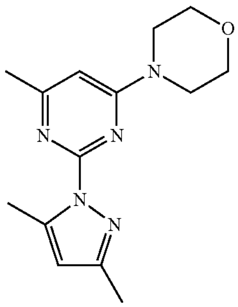 [SMILES: Cc1cc(N2CCOCC2)nc(-n2nc(C)cc2C)n1] | | | ¹H-NMR (CDCl₃): 2.32 (3H, s), 2.47 (3H, s), 2.61 (3H, s), 3.62-3.65 (4H, m), 3.78-3.81 (4H, m), 5.98 (1H, s), 6.23 (1H, s) | 79% |
| 14 | 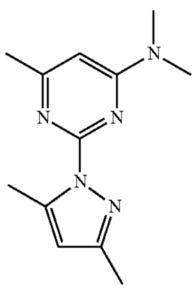 | | | ¹H-NMR (CDCl₃): 2.32 (3H, s), 2.46 (3H, s), 2.64 (3H, s), 3.12 (6H, 8), 5.97 (1H, s), 6.14 (1H, s) | 55% |
| 4 | 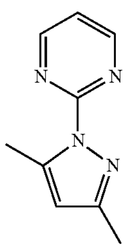 | | | 1H-NMR (DMSO-d6); 2.20 (3H, s), 2.55 (3H s), 6.14 (1H, s), 7.42 (1H, t), 8.85 (2H, d) | 69% |
| 23 | 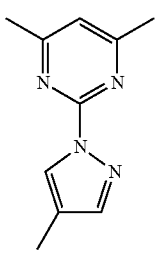 | | | ¹H-NMR (CDCl₃): 2.16 (3H, s), 2.53 (6H, s), 6.88 (1H, s), 7.62 (1H, s), 8.36 (1H, s) | 57% |
| 41 | 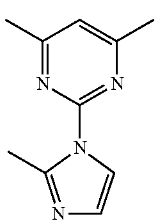 | | | ¹H-NMR (CDCl₃): 2.50 (6H, s), 2.82 (3H, s), 6.89 (1H, s), 6.95 (1H, d), 7.86 (1H, d) | 67% |
| 42 | 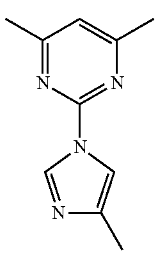 | | | ¹H-NMR (CDCl₃): 2.28 (3H, s), 2.48 (6H, s), 6.87 (1H, s), 7.27 (1H, s), 7.60 (1H, s) | 14% |

Synthesis Example 6-1

Synthesis of N-(pyrimidin-2-yl)-2,6-dimethylmorpholine

In a 100 mL recovery flask, 2-chloropyrimidine (1 g, 8.73 mmol), 2,6-dimethyl morpholine (cis:trans mixture, 1.106 g, 9.60 mmol), N,N-diisopropyl-N-ethylamine (1.241 g, 9.60 mmol), and ethanol (17.46 mL) were added and refluxed for seven hours. Upon completion of the reaction, the solvent was distilled off, and saturated sodium bicarbonate was added thereto. The resulting mixture was extracted with ethyl acetate twice, and the organic phase was washed with saturated brine and dried over magnesium sulfate. The solvent was distilled off under reduced pressure and the residue was purified by silica gel column chromatography (hexane:ethyl acetate=20:1→1:2) to give the title compound (1.29 g, 76%, cis:trans mixture).
(cis:trans Mixture)
$^1$H-NMR (CDCl$_3$): 1.26 (6H, d), 2.60 (2H, dd), 3.61-3.69 (2H, m), 4.52-4.56 (2H, m), 6.50 (1H, t), 8.32 (2H, d).
$^1$H-NMR (CDCl$_3$): 1.24 (6H, d), 3.52 (2H, dd), 3.90 (2H, dd), 4.07-4.11 (2H, m), 6.48 (1H, t), 8.30 (2H, d).

Synthesis Example 6-2

Synthesis of N-(4,6-dimethylpyrimidin-2-yl)-3,5-dimethylpiperidine (Compound 45)

In a similar manner to Synthesis Example 6-1 except that 2-chloro-4,6-dimethylpyrimidine and 3,5-dimethylpiperidine were used instead of 2-chloropyrimidine and 2,6-dimethylmorpholine, respectively, N-(4,6-dimethylpyrimidin-2-yl)-3,5-dimethylpiperidine (Compound 45) was obtained (yield 97%).
(cis:trans Mixture)
$^1$H-NMR (CDCl$_3$): 0.73-0.82 (1H, m), 0.94 (6H, d), 1.58-1.64 (2H, m), 1.76-1.88 (1H, m), 2.27 (6H, s), 2.20-2.30 (2H, m), 4.75-4.85 (2H, m), 6.20 (1H, s).
$^1$H-NMR (CDCl$_3$): 0.94 (6H, d), 1.44-1.46 (2H, m), 1.91-1.97 (2H, m), 3.42-3.47 (2H, m), 3.80-3.86 (1H, m), 6.18 (1H, s).

Hereinbelow, Formulation Examples of the skin external preparation of the present invention are shown. In each Formulation Example, one or more compounds of the present invention can be used. Any of the skin external preparations shown in Formulation Examples below exerts a whitening effect because of the by the addition of the compound of the present invention.

Formulation Example 1

Cream

| (Formulation) | |
|---|---|
| Stearic acid | 5.0% by mass |
| Stearyl alcohol | 4.0 |
| Isopropyl myristate | 18.0 |
| Glyceryl monostearate | 3.0 |
| Propylene glycol | 10.0 |
| Compound of the present invention | 0.1 |
| Caustic potash | 0.2 |
| Sodium bisulfite | 0.05 |
| Preservative | q.s. |
| Fragrance | q.s. |
| Ion-exchanged water | balance |

(Production Method)
Propylene glycol and caustic potash were dissolved in ion-exchanged water, and the resulting mixture was heated to and maintained at 70° C. (aqueous phase). Other components were mixed and melted by heat, and maintained at 70° C. (oil phase). The oil phase was gradually added to the aqueous phase, and after the complication of the addition, the resulting mixture was maintained at 70° C. for some time to allow a reaction to proceed. Subsequently, the mixture was homogeneously emulsified by a homomixer, and cooled to 30° C. while thoroughly stirring.

Formulation Example 2

Cream

| (Formulation) | |
|---|---|
| Stearic acid | 5.0 by mass % |
| Sorbitan monostearate | 2.5 |
| Polyoxyethylene (20) sorbitan monostearate | 1.5 |
| Arbutin | 7.0 |
| Sodium bisulfite | 0.03 |
| Propylene glycol | 10.0 |
| Compound of the present invention | 0.05 |
| Glyceryl trioctanoate | 10.0 |
| Squalene | 5.0 |
| Octyl p-dimethylaminobenzoate | 3.0 |
| Disodium ethylenediaminetetraacetate | 0.01 |
| Ethylparaben | 0.3 |
| Fragrance | q.s. |
| Ion-exchanged water | balance |

(Production Method)
Propylene glycol and disodium ethylenediaminetetraacetate were dissolved in ion-exchanged water and the resulting mixture was maintained at 70° C. (aqueous phase). Other components were mixed and melted by heat, and maintained at 70° C. (oil phase). The oil phase was gradually added to the aqueous phase. The mixture was preliminarily emulsified at 70° C., homogeneously emulsified by a homomixer, and then cooled to 30° C. while thoroughly stirring.

Formulation Example 3

Cream

| (Formulation) | |
|---|---|
| Solid paraffin | 5.0% by mass |
| Beeswax | 10.0 |
| Petrolatum | 15.0 |
| Liquid paraffin | 41.0 |
| Glyceryl monostearate | 2.0 |
| POE (20) sorbitan monolaurate | 2.0 |
| Soap powder | 0.1 |
| Borax | 0.2 |
| Compound of the present invention | 0.05 |
| Sodium bisulfite | 0.03 |

-continued

| (Formulation) | |
|---|---|
| Ethylparaben | 0.3 |
| Fragrance | q.s. |
| Ion-exchanged water | balance |

(Production Method)

Powder soap and borax were added to ion-exchanged water and dissolved with heat, and the resulting mixture was maintained at 70° C. (aqueous phase). Other components were mixed and melted by heat, and maintained at 70° C. (oil phase). While stirring, the oil phase was gradually added to the aqueous phase to allow a reaction to proceed. Upon completion of the reaction, the mixture was homogeneously emulsified by a homomixer, and then cooled to 30° C. while thoroughly stirring.

Formulation Example 4

Milky Lotion

| (Formulation) | |
|---|---|
| Stearic acid | 2.5% by mass |
| Cetyl alcohol | 1.5 |
| Petrolatum | 5.0 |
| Liquid paraffin | 10.0 |
| POE (10) monooleate | 2.0 |
| Polyethylene glycol 1500 | 3.0 |
| Triethanolamine | 1.0 |
| Carboxyvinyl polymer | 0.05 |
| Compound of the present invention | 0.01 |
| Sodium bisulfite | 0.01 |
| Ethylparaben | 0.3 |
| Fragrance | q.s. |
| Ion-exchanged water | balance |

(Production Method)

Carboxyvinyl polymer was dissolved in a small amount of ion-exchanged water (phase A). Polyethylene glycol 1500 and triethanolamine were added to the remaining ion-exchanged water and dissolved with heat, and the resulting mixture was maintained at 70° C. (aqueous phase). Other components were mixed and melted by heat, and maintained at 70° C. (oil phase). The oil phase was added to the aqueous phase and preliminarily emulsified. After addition of phase A, the resulting mixture was homogeneously emulsified by a homomixer and then cooled to 30° C. while thoroughly stirring.

Formulation Example 5

Milky Lotion

| (Formulation) | |
|---|---|
| Microcrystalline wax | 1.0% by mass |
| Beeswax | 2.0 |
| Lanolin | 20.0 |
| Liquid paraffin | 10.0 |
| Squalane | 5.0 |
| Sorbitan sesquioleate | 4.0 |
| POE (20) sorbitan monooleate | 1.0 |

| (Formulation) | |
|---|---|
| Propylene glycol | 7.0 |
| Compound of the present invention | 1.0 |
| Sodium bisulfite | 0.01 |
| Ethylparaben | 0.3 |
| Fragrance | q.s. |
| Ion-exchanged water | balance |

(Production Method)

Propylene glycol was added to ion-exchanged water, and the resulting mixture was heated and maintained at 70° C. (aqueous phase). Other components were mixed and melted by heat, and maintained at 70° C. (oil phase). While stirring the oil phase, the aqueous phase was gradually added to the oil phase. The resulting mixture was homogeneously emulsified by a homomixer and then cooled to 30° C. while thoroughly stirring.

Formulation Example 6

Jelly

| (Formulation) | |
|---|---|
| 95% Ethanol | 10.0% by mass |
| Dipropylene glycol | 15.0 |
| POE (50) oleyl ether | 2.0 |
| Carboxyvinyl polymer | 1.0 |
| Caustic soda | 0.15 |
| L-arginine | 0.1 |
| Compound of the present invention | 5.0 |
| Sodium 2-hydroxy-4-methoxybenzophenone sulfonate | 0.05 |
| Trisodium ethylenediaminetetraacetate dihydrate | 0.05 |
| Methylparaben | 0.2 |
| Fragrance | q.s. |
| Ion-exchanged water | balance |

(Production Method)

Carboxyvinyl polymer was homogeneously dissolved in ion-exchanged water. Separately, the compound of the present invention and POE (50) oleyl ether were dissolved in 95% ethanol and then added to the aqueous phase. After addition of the remaining components, the resulting mixture was neutralized by caustic soda and L-arginine to increase the viscosity.

Formulation Example 7

Essence

| (Formulation) | |
|---|---|
| (Phase A) | |
| Ethyl alcohol (95%) | 10.0% by mass |
| POE (20) octyldodecanol | 1.0 |
| Pantothenyl ethyl ether | 0.1 |
| Compound of the present invention | 2.0 |
| Methylparaben | 0.15 |
| (Phase B) | |
| Potassium hydroxide | 0.1 |

| (Formulation) | |
|---|---|
| (Phase C) | |
| Glycerol | 5.0 |
| Dipropylene glycol | 10.0 |
| Sodium bisulfite | 0.03 |
| Carboxyvinyl polymer | 0.2 |
| Purified water | balance |

(Production Method)

Each of Phase A and Phase C was homogeneously dissolved, and Phase A was added to Phase C to be solubilized. After addition of Phase B, the resulting mixture was packed in a container.

Formulation Example 8

Pack

| (Formulation) | |
|---|---|
| (Phase A) | |
| Dipropylene glycol | 5.0% by mass |
| POE (60) hydrogenated castor oil | 5.0 |
| (Phase B) | |
| Compound of the present invention | 0.05 |
| Olive oil | 5.0 |
| Tocopherol acetate | 0.2 |
| Ethylparaben | 0.2 |
| Fragrance | 0.2 |
| (Phase C) | |
| Sodium bisulfite | 0.03 |
| Polyvinyl alcohol (saponification degree of 90 and polymerization degree of 2,000) | 13.0 |
| Ethanol | 7.0 |
| Purified water | balance |

(Production Method)

Each of Phase A, Phase B, and Phase C was homogeneously dissolved, and Phase B was added to Phase A to be solubilized. After addition of Phase C, the resulting mixture was packed in a container, Formulation Example 9

Solid Foundation

| (Formulation) | |
|---|---|
| Talc | 43.1% by mass |
| Kaolin | 15.0 |
| Sericite | 10.0 |
| Zinc oxide | 7.0 |
| Titanium dioxide | 3.8 |
| Yellow iron oxide | 2.9 |
| Black iron oxide | 0.2 |
| Squalane | 8.0 |
| Isostearic acid | 4.0 |
| POE sorbitan monooleate | 3.0 |
| Isocetyl octanoate | 2.0 |
| Compound of the present invention | 0.5 |

| (Formulation) | |
|---|---|
| Preservative | q.s. |
| Fragrance | q.s. |

(Production Method)

Powdery components from talc to black iron oxide shown above were thoroughly mixed by a blender. To this mixture were added oily components from squalane to isocetyl octanoate shown above, the compound of the present invention, preservative, and fragrance. The resulting mixture was thoroughly kneaded, packed in a container, and then formed.

Formulation Example 10

Emulsion Foundation (Cream-Type)

| (Formulation) | |
|---|---|
| (Powder part) | |
| Titanium dioxide | 10.3% by mass |
| Sericite | 5.4 |
| Kaolin | 3.0 |
| Yellow iron oxide | 0.8 |
| Red iron oxide | 0.3 |
| Black iron oxide | 0.2 |
| (Oil phase) | |
| Decamethylcyclopentasiloxane | 11.5 |
| Liquid paraffin | 4.5 |
| Polyoxyethylene-modified dimethylpolysiloxane | 4.0 |
| Compound of the present invention | 0.5 |
| (Aqueous phase) | |
| Purified water | 50.0 |
| 1,3-Butylene glycol | 4.5 |
| Sorbitan sesquioleate | 3.0 |
| Preservative | q.s. |
| Fragrance | q.s. |

(Production Method)

The aqueous phase was stirred with heat and then the powder part, which had been fully mixed and pulverized, was added. The mixture was treated with a homomixer and then the oil phase, which had been mixed with heat, was added. The mixture was treated with a homomixer and then fragrance was added while stirring. The mixture thus obtained was cooled to room temperature.

Formulation Example 11

Lotion

| | | |
|---|---|---|
| (1) Compound of the present invention | 0.05% by mass |
| (2) Aspartic acid | 1.0 |
| (3) Tocopherol acetate | 0.01 |
| (4) Glycerol | 4.0 |
| (5) 1,3-Butyleneglycol | 4.0 |
| (6) Ethanol | 8.0 |
| (7) POE (60) hydrogenated castor oil | 0.5 |
| (8) Methylparaben | 0.2 |
| (9) Citric acid | 0.05 |
| (10) Sodium citrate | 0.1 |

-continued

| | |
|---|---|
| (11) Fragrance | 0.05 |
| (12) Purified water | balance |

(Production Method)

(2), (4), (5), (9), and (10) were dissolved in (12) to provide a purified water solution. Separately, (1), (3), (7), (8), and (11) were dissolved in (6), and the resulting mixture was added to the aforementioned the purified water solution to be solubilized. The mixture thus obtained was filtrated to provide a lotion.

Formulation Example 12

Lotion

| A: Alcohol phase | |
|---|---|
| Ethanol | 5.0% by mass |
| POE oleyl ether | 2.0 |
| 2-Ethylhexyl-p-dimethylaminobenzoate | 0.18 |
| Compound of the present invention | 0.1 |
| Fragrance | 0.05 |
| B: Aqueous phase | |
| 1,3-Butylene glycol | 9.5 |
| 2-O-Ethyl ascorbic acid | 0.5 |
| Sodium pyrrolidonecarboxylate | 0.5 |
| Whey extract | 5.0 |
| Nicotinamide | 0.3 |
| Glycerol | 5.0 |
| Hydroxypropyl-β-cyclodextrin | 1.0 |
| Trisodium hydroxyethylethylenediamine triacetate | 1.0 |
| Lysine | 0.05 |
| Tranexamic acid | 1.0 |
| Purified water | balance |

(Production Method)

Alcohol phase A was added to Aqueous phase B and solubilized to provide a lotion.

Formulation Example 13

Cream (Whitening)

| | |
|---|---|
| Trans-4-(trans-aminomethylcyclohexanecarbonyl) aminomethylcyclohexanecarboxylic acid hydrochloride | 1.0% by mass |
| Potassium 4-methoxysalicylate | 1.0 |
| 3-O-Ethylascorbic acid | 1.0 |
| Linoleic acid | 0.3 |
| Sodium lipoate | 1.0 |
| Compound of the present invention | 3.0 |
| Coenzyme Q10(CoQ10) | 0.03 |
| Petrolatum | 2.0 |
| Dimemylpolysiloxane | 2.0 |
| Ethanol | 5.0 |
| Behenyl alcohol | 0.5 |
| Batyl alcohol | 0.2 |
| Glycerol | 7.0 |
| 1,3-Butylene glycol | 5.0 |
| Polyethylene glycol 20000 | 0.5 |
| Jojoba oil | 3.0 |
| Squalane | 2.0 |
| Phytosteryl hydroxystearate | 0.5 |
| Pentaerythritol tetra(2-ethylhexanoate) | 1.0 |
| Polyoxyethylene hydrogenated castor oil | 1.0 |
| Potassium hydroxide | 0.1 |

-continued

| | |
|---|---|
| Sodium pyrosulfite | 0.01 |
| Sodium hexametaphosphate | 0.05 |
| Stearyl glycyrrhetinate | 0.1 |
| Pantothenyl ethyl ether | 0.1 |
| Arbutin | 7.0 |
| Tranexamic acid | 2.0 |
| Tocopherol acetate | 0.1 |
| Sodium hyaluronate | 0.05 |
| p-Hydroxybenzoate ester | q.s. |
| Trisodium edetate | 0.05 |
| 4-t-Butyl-4'-methoxydibenzoylmethane | 0.1 |
| Glyceryl diparamethoxycinnamate mono-2-ethylhexanoate | 0.1 |
| Yellow iron oxide | q.s. |
| Xanthan gum | 0.1 |
| Carboxyvinyl polymer | 0.2 |
| Purified water | balance |

Formulation Example 14

Two-Phase Cream (Sunscreen)

| | |
|---|---|
| Tranexamic acid | 2.0% by mass |
| Potassium 4-methoxysalicylate | 1.0 |
| Compound of the present invention | 0.03 |
| Dimethylpolysiloxane | 5.0 |
| Decamethylcyclopentasiloxane | 25.0 |
| Trimethylsiloxysilicate | 5.0 |
| Polyoxyethylene/methylpolysiloxane copolymer | 2.0 |
| Dipropylene glycol | 5.0 |
| Dextrin palmitate-coated fine-particle zinc oxide (60 nm) | 15.0 |
| Dipotassium glycyrrhizinate | 0.02 |
| Glutathione | 1.0 |
| Thiotaurine | 0.05 |
| *Sophora flavescens* extract | 1.0 |
| Paraben | q.s. |
| Phenoxyethanol | q.s. |
| Trisodiiun edetate | q.s. |
| 2-Ethylhexyl p-methoxycinnamate | 7.5 |
| Dimethyldistearylammonium hectorite | 0.5 |
| Spherical poly(alkyl acrylate) powder | 5.0 |
| Butylethylpropanediol | 0.5 |
| Purified water | balance |
| Fragrance | q.s. |

Formulation Example 15

Gel (Whitening)

| | |
|---|---|
| Potassium 4-methoxysalicylate | 0.1% by mass |
| Rucinol | 0.3 |
| Dihydrolipoic acid | 1.0 |
| *Lamium album* var. *barbatum* | 0.1 |
| Dimethylpolysiloxane | 5.0 |
| Glycerol | 2.0 |
| 1,3-Butylene glycol | 5.0 |
| Polyethylene glycol 1500 | 3.0 |
| Polyethylene glycol 20000 | 3.0 |
| Cetyl octanoate | 3.0 |
| Citric acid | 0.01 |
| Sodium citrate | 0.1 |
| Sodium hexametaphosphate | 0.1 |
| Compound of the present invention | 1.0 |
| Dipotassium glycyrrhizinate | 0.1 |
| Ascorbyl glucoside | 2.0 |
| Tocopherol acetate | 0.1 |
| *Scutellaria baicalensis* extract | 0.1 |

-continued

| | |
|---|---|
| Saxifraga stolonifera extract | 0.1 |
| Trisodium edetate | 0.1 |
| Xanthan gum | 0.3 |
| Acrylic acid/alkyl methacrylate copolymer (Pemulen TR-2) | 0.05 |
| Agar powder | 1.5 |
| Phenoxyethanol | q.s. |
| Dibutylhydroxytoluene | q.s. |
| Purified water | balance |

Formulation Example 16

Pack (Moisturizing)

| | |
|---|---|
| Trans-4-aminomethylcyclohexanecarboxylic acid methylamide hydrochloride | 10.0% by mass |
| Dihydrolipoamide | 1.0 |
| Rosa multiflora fruit extract | 0.1 |
| Ethanol | 10.0 |
| 1,3-Butylene glycol | 6.0 |
| Polyethylene glycol 4000 | 2.0 |
| Olive oil | 1.0 |
| Macadamia nut oil | 1.0 |
| Phytosteryl hydroxystearate | 0.05 |
| Lactic acid | 0.05 |
| Sodium lactate | 0.1 |
| Disodium L-ascorbyl sulfate | 0.1 |
| Compound of the present invention | 0.5 |
| Potassium 2-L-Ascorbyl α-tocopheryl phosphate | 0.1 |
| Vitamin E acetate | 0.1 |
| Fish collagen | 0.1 |
| Sodium chondroitin sulfate | 0.1 |
| Sodium carboxymethyl cellulose | 0.2 |
| Polyvinyl alcohol | 12.0 |
| p-Hydroxybenzoate | q.s. |
| Purified water | balance |
| Fragrance | q.s. |

Formulation Example 17

Lotion (Moisturizing)

| | |
|---|---|
| Tranexamic acid | 1.0% by mass |
| Potassium 4-methoxysalicylate | 1.0 |
| Lipoic acid | 10.0 |
| Hamamelis | 0.1 |
| Silica-coated zinc oxide | 0.1 |
| Hypotaurine | 0.1 |
| Sophora flavescens extract | 0.1 |
| Peach kernel extract | 0.1 |
| Beech sprout extract | 0.1 |
| Retinol | 0.1 |
| Compound of the present invention | 0.01 |
| Ethyl alcohol | 5.0 |
| Glycerol | 1.0 |
| 1,3-Butylene glycol | 5.0 |
| Polyoxyethylene polyoxypropylene decyltetradecyl ether | 0.2 |
| Sodium hexametaphosphate | 0.03 |
| Trimethylglycine | 1.0 |
| Sodium polyaspartate | 0.1 |
| Potassium 2-L-Ascprbyl α-tocopheryl phosphate | 0.1 |
| Thiotaurine | 0.1 |
| Green tea extract | 0.1 |
| Peppermint extract | 0.1 |
| Iris root extract | 1.0 |

| | |
|---|---|
| Trisodium EDTA | 0.1 |
| Carboxyvinyl polymer | 0.05 |
| Potassium hydroxide | 0.02 |
| Phenoxyethanol | q.s. |
| Purified water | balance |
| Fragrance | q.s. |

What is claimed is:

1. A method for inhibiting melanin production comprising topically applying to skin of a human in need of such inhibition a preparation comprising an effective amount of a heterocyclic compound represented by formula (1) or a pharmacologically acceptable salt thereof:

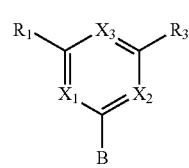

(1)

wherein
$X_1=X_2=N$ and $X_3=CR_2$, or $X_1=CR_2$ and $X_2=X_3=N$;
$R_1$, $R_2$, and $R_3$ are each independently H, $C_{1-6}$ alkyl, $C_{1-6}$ alkoxy, SH, OH, or $NR_bR_c$, wherein $R_b$ and $R_c$ are each independently H, $C_{1-6}$ alkyl, or hydroxy-$C_{1-6}$ alkyl, or wherein $NR_bR_c$ forms a saturated or unsaturated 5- or 6-membered hetero ring;
B is a group represented by formula (B1):

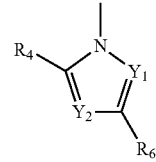

(B1)

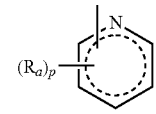

(B2)

wherein
$Y_1$ is N, and $Y_2$ is $CR_5$;
$R_4$, $R_5$, and $R_6$ are each independently H, $C_{1-6}$ alkyl, $C_{1-6}$ alkoxy, $C_{2-7}$ acyloxy, OH, amino, —NH-A, —NHCO-A, or —NHCOCH$_2$-A, wherein A is $C_{1-6}$ alkyl, phenyl, or a 5- or 6-membered heterocyclic group, or
$R_4$ and $R_5$, or $R_5$ and $R_6$ together form a 5- or 6-membered hydrocarbon ring condensed with the hetero ring to which $R_4$, $R_5$, and $R_6$ are bound;
with the proviso that
at least one of $R_1$, $R_3$, $R_4$, and $R_6$ is a group other than $C_{1-3}$ alkyl in the case where $X_1=X_2=Y_1=N$ and $X_3=CR_2$.

2. The method of claim 1, wherein the heterocyclic compound acts as a skin-whitening agent.

* * * * *